United States Patent [19]

Espevik et al.

[11] Patent Number: 5,532,216
[45] Date of Patent: Jul. 2, 1996

[54] NEUTRALIZATION OF NON-LIPOPOLYSACCHARIDE COMPOUNDS BY BACTERICIDAL/PERMEABILITY-INCREASING PROTEIN

[75] Inventors: Terje Espevik, Trondheim, Norway; Marian N. Marra, San Mateo, Calif.

[73] Assignee: Incyte Pharmaceuticals, Inc., Palo Alto, Calif.

[21] Appl. No.: 267,139

[22] Filed: Jun. 28, 1994

Related U.S. Application Data

[63] Continuation-in-part of Ser. No. 265,088, Jun. 24, 1994, abandoned.

[51] Int. Cl.$^6$ ............................ A61K 38/00; C07K 17/00
[52] U.S. Cl. ................................ 514/21; 514/8; 514/12; 530/350; 530/303; 530/397
[58] Field of Search ................................ 514/21, 8, 12; 530/350, 303, 397

[56] References Cited

U.S. PATENT DOCUMENTS

| | | | |
|---|---|---|---|
| 4,950,600 | 8/1990 | Tanaka et al. | 435/178 |
| 5,089,274 | 2/1992 | Marra et al. | 424/534 |
| 5,348,942 | 9/1994 | Little, II et al. | 514/12 |

OTHER PUBLICATIONS

Otterelei et al, *Journal of Immunotherapy*, vol. 10, No. 4, pp. 286–291, 1991.

Otterelei et al, *Infection and Immunity*, vol. 61, No. 5, pp. 1917–1925, May 1993.

Lim, *Science*, vol. 210, pp. 908–910, 21 Nov., 1980.

Dentener et al., "Antagonistic Effects of Lipopolysaccharide Binding Protein and Bactericidal/Permeability–Increasing Protein on Lipopolysaccharide–Induced Cytokine Release by Mononuclear Phagocytes: Competition for Binding to Lipopolysaccharide," *J. Immuno.* (1993) 151(8):4258–65.

Heumann et al., "Competition between Bactericidal/Permeability–Increasing Protein and Lipopolysaccharide–Binding Protein for Lipopolysaccharide Binding to Monocytes," *J. Infect. Diseases* (1993) 167:1351–57.

Capodici et al., "Effect of Lipopolysaccharide (LPS) Chain Length on Interactions of Bactericidal/Permeabilty–Increasing Protein and its Bioactive 23–Kilodalton $NH_2$–Terminal Fragment with Isolated LPS and Intact *Proteus mirabilis* and *Escherichia coli,*" *Infect. Immun.* (1994) 62(1):259–65.

Marra et al., "The Role of Bactericidal/Permeability–Increasing Protein as a Natural Inhibitor of Bacterial Endotoxin," *J. Immunol.* (1992) 148(2):532–7.

Weiss et al., "Human Bactericidal/Permeability–Increasing Protein and a Recombinant $NH_2$–Terminal Fragment Cause Killing of Serum–resistant Gram–negative Bacteria in Whole Blood and Inhibit Tumor Necrosis Factor Release Induced by the Bacteria," *J. Clin. Invest.* (1992)90:1122–30.

Otterlei et al., "Similar Mechanisms of Action of Defined Polysaccharides and Lipopolysaccharides: Characterization of Binding and Tumor Necrosis Factor Alpha Induction," *Infect. Immun.* (1993) 61(5):1917–25.

Marra et al., "Bactericidal/Permeability–Increasing Protein has Endotoxin–Neutralizing Activity," *J. Immuno.* (1980) 144(2):662–666.

Lim et al., "Microencapsulated Islets as Bioartificial Endocrine Pancreas," *Science* (1980) 210:908–910.

O'Shea et al., "Prolonged Survival of Transplated Islets of Langerhans Encapsulated in a Biocompatible Membrane," *Biochem. Biophys. ACTA* (1984) 804:133–136.

Sun et al., "Microencapsulated Cells as Hormone Delivery Systems," *CRC Critical Rev. Thera. Drug Carrier Systems* (1987) 4:1–12.

Sun et al., "Encapsulated Versus Modified Endocrine Cells for Organ Replacement," *Trans Am Soc Artif Intern Organs* (1987) 33:787–790.

Tze et al., "Biocompatibility and Immunological Studies of Microencapsulation with Cross–Linked Alginate Capsules," *Transplanation* (1982) 33(5):563–564.

Miura et al., "Synthesis and Secretion of Protein by Hepatocytes Entrapped within Calcium Alginate," *Artificial Organs* (1986) 10(6):460–465.

Darquy et al., "Microencapsulation of Parathyroid Cells as a Bioartificial Parathyroid," *Trans Am Soc Artif Intern Organs* (1987) 33:356–358.

Otterlei et al., "Induction of Cytokine Production from Human Monocytes Stimulated with Alginate," *J. Immuno.* (1991) 10:286–291.

Sun et al., *Topics in Pharmaceutical Science*, Elsevier Science Publishers, Amsterdam, (1985) p. 93.

Goosen et al., *Biotechnol. Bioeng.* (1985) 27:146.

Soon–Shiong et al., "Successful Reversal of Spontaneous Diabetes in Dogs by Intraperitoneal Microencapsulated Islets," *Transplantation* (1992) 54:769–774.

Tompkins et al., *Biotechnol. Bioeng.* (1988) 31:11.

*Primary Examiner*—Christina Y. Chan
*Assistant Examiner*—Abdel A. Mohamed
*Attorney, Agent, or Firm*—Karl Bozicevic; Carol L. Francis; Fish & Richardson

[57] ABSTRACT

Bactericidal/permeability-increasing protein (BPI) is useful to neutralize non-lipopolysaccharide compounds capable of stimulating TNF production and has application in vitro and in vivo for therapeutics and prophylactic treatment. This use of BPI can be combined with the administration of materials, such as an enzyme, microorganism, living cells or cell fractions, encapsulated in alginate gels.

13 Claims, 2 Drawing Sheets

NEUTRALIZATION OF NON-LIPOPOLYSACCHARIDE COMPOUNDS BY BACTERICIDAL/PERMEABILITY-INCREASING PROTEIN

CROSS-REFERENCE TO RELATED APPLICATIONS

This application is a continuation-in-part of a patent application entitled "Neutralization of Non-Lipopolysaccharide Compounds By Bactericidal/Permeability-Increasing Protein," U.S. application Ser. No. 08/265,088, filed Jun. 24, 1994, now abandoned.

FIELD OF THE INVENTION

The present invention relates to neutralization of non-lipopolysaccharide compounds by Bactericidal/Permeability-Increasing Protein (BPI), and use thereof in therapeutic and prophylactic applications.

BACKGROUND OF THE INVENTION

Bactericidal/permeability-increasing protein (BPI) neutralizes bactericidal lipopolysaccharides (LPS) as described in Marta et al. U.S. Pat. No. 5,089,274; Dentener et al. (Oct. 15, 1993) *J Immunol* 151: 4258– 4265; Heumann et al. (1993) *J Infectious Diseases* 167:1351–1357 and Capadici et al. (January 1994) *Infection & Immunity.* 62(1):259–265. Bactericidal LPS is a powerful stimulator of the inflammatory response in vivo. In vitro LPS activation of cellular and humoral components of the inflammatory response is blocked by BPI.

Many of the patho-physiologic effects of endotoxin appear to be mediated by the activation of mononuclear cells with the subsequent generation of the proinflammatory cytokines, TNF-alpha and interleukin-1. Macrophage responsiveness to endotoxin varies over time and depends upon several factors (Morrison, D. C. and J. L. Ryan (1987) *Ann. Rev. Med.* 38:417–432). Endotoxin-signaling pathways within the macrophage are complex and not entirely understood. However, it has become increasingly apparent that endotoxin signaling is initiated with its attachment to the CD14 antigen on the macrophage cell surface (Wright et al. (1990) *Science* 249:1431–1433). Endogenous proteins which facilitate the delivery of endotoxin to the macrophage cell surface, such as LPS-binding protein (LBP) (Schumann et al (1990) *Science* 249:1429–1431) stimulate the monocyte/macrophage cell line to produce proinflammatory cytokines and activate a cascade of host-derived inflammatory mediators.

In contrast, BPI blocks endotoxin delivery to the CD14 antigen (Marra et al (1990) *J. Immunol.* 144:662–666; Marra et al. (1.992) *J. Immunol.* 148:537). BPI binding to endotoxin has been shown to attenuate cytokine release by mononuclear cells and to inhibit endotoxin mediated activation of neutrophils (Marra et al. (1990), supra; Marra et al. (1992), supra; Weiss et al (1992) *J. Clin. Invest.* 90:1122–1130; Heumann et al. (1993) *J. Infect. Dis.* 176:1351–1357).

Most of the various activities of endotoxin have been attributed to the lipid A domian of LPS (Morrison and Ulevitch (1978) *Amer. J. Pathol.* 93:525). Marra et al. have shown that BPI binds the lipid A domain of endotoxin, thereby preventing subsequent activation of neutrophils (Marra et al. (1990) *J. Immunol* 144:662). Capodici eta. have reported that BPI blocks the effects of isolated LPS and LPS on *Proteus mirabills* and *E. Coli,* which only have the lipid A component in common (*Infect. Immun.* (1994) 62:25–65).

An example of an in vitro system used to study LPS-mediated cellular activation in vitro is the release of tumor necrosis factor (TNF) and interleukin-1 (IL-1) from macrophages in response to LPS exposure. TNF and IL-1 are cytokines which stimulate fibroblast growth. (LeJ. Vilcek, J. (1987) *Lab Invest* 56:234). TNF is a potent stimulator of neutrophils.

Polysaccharides other than LPS have also been reported to have immunostimulating activity including stimulation of macrophage function and TNF release. For example, Otterlei et al. (May 1993) *Infection and Immunity* 61(5):1917–1925, describe the similarity of action of defined polysaccharides and lipopolysaccharides in TNF production.

Entrapment within alginate gel with divalent cation (calcium, barium, strontium or the like) is a widely used technique for immobilization of living cells (Scott, C. D., (1987) *Enzyme Microb Technol* 9:66). Microencapsulation of hormone-producing cells in calcium alginate has been used for treatment of (1) diabetes mellitus (Lim et al., (1980) *Science* 21:908; O'Shea et al., (1984) *Biochem Biophys Acta* 804:133; Goosen et al., (1985) *Biotech Bioeng* 27:146; Sun et al., "Topics in pharmaceutical science", (1985) Amsterdam, Elsevier Science Publishers B.V. pp.93; Sun, A. M., (1987) *Trans Am Soc Artif Organs* 33787; Sun et al., (1987) *CRC Crit Rev Ther Drug Carrier Sys* 4: 1–12; Tze et al., ( 1982) *Transplantation* 33:563; and Soon-Shiong et al., (1992) *Transplantation* 54:769–774; (2) liver diseases (Miura et al., (1986) *Artif Organs* 10:460 and Tompkins et al., (1988) *Biotechnol Bioeng* 31:11); and (3) parathyroid diseases (Darquay et al., (1987) *Trans Am Soc Artif Inter Organs* 33:365).

Alginates are polysaccharides composed of homopolymeric gel-forming regions of beta-D-mannuronic (M) and alpha-L-glucuronic (G) acid also called "M-blocks" and "G-blocks", respectively, interspaced with regions of mixed sequence ("M-G-blocks") .

The main problem in vivo with alginate capsules is that they induce macrophages and like cells to release cytokines which cause fibroblast overgrowth resulting in failure of encapsulated cells (Sun, A. M., (1987) *Trans Am Soc Artif Organs* 33:787). Alginates simulate macrophages to release cytokines such as TNF, IL-1, and IL-6. The M-block and MG-blocks but not G-blocks strongly induce cytokine production (Otterlei et al, (1991) *J Immunotherapy* 10:286–291). If alginates are to be used as a matrix for implanted materials, such as hormone-producing cells, it is important that they do not cause inflammatory reactions.

According to Soon-Shiong et al, "Investigators have long sought to reverse insulin-dependent diabetes by a simple injection of immuno-protected insulin-secreting cells without immunosuppression" (Soon-Shiong et al, (1992) *Transplantation,* 54:769).

Encapsulation of transplanted insulin-producing (islet) cells provides a method to prevent direct exposure of the host's immune system to the transplanted cells, and this decreases the requirement for immunosuppressants.

Up until the present invention, there has been no suggestion that BPI could have neutralizing activity against molecules other than LPS which can activate inflammatory cells in vitro or in vivo. Data first provided in this application demonstrate that BPI inhibits human monocyte activation (e.g., TNF production) induced by mannuronic acid polymers. Thus, it has been discovered that BPI is useful in preventing and arresting a deleterious inflammatory response to alginate-encapsulated cells for transplant.

In contrast to the prior art, the present invention has demonstrated that BPI can inhibit non-LPS-caused immunostimulation, such as stimulation of macrophage function and TNF release. Thus, BPI has a novel and distinct use in the therapeutic and prophylactic treatment of non-LPS-stimulated inflammation. Furthermore, the invention provides a composition comprising BPI and a non-lipopolysaccharide, such as an alginate gel, which composition inhibits inflammation ordinarily caused by the alginate. Such a composition represents an improvement over the state of the art.

SUMMARY OF THE INVENTION

The present invention is directed to a method of inhibiting (neutralizing) non-lipopolysaccharide-mediated stimulation of host inflammatory cells by administering bactericidal/permeability-increasing protein (BPI). The method comprises administering to the host, in the presence of a cell-stimulating amount of a non-lipopolysaccharide, a BPI protein in an amount effective to inhibit host inflammatory cell stimulation.

The invention is also directed to inhibiting of non-lipopolysaccharide-mediated tumor necrosis factor (TNF), interleukin-1 (IL-1) or interleukin-6 (IL-6) production by human mononuclear cells, in the presence of a cell-stimulating amount of a non-lipopolysaccharide, which comprises administering to the host a BPI protein in an amount effective to inhibit TNF, IL-1 or IL-6 production by the host inflammatory cells.

The non-lipopolysaccharide can comprise an alginate gel used to immobilize enzymes, micro-organisms, living cells, organelles and cell fractions, and the like, such as hormone-producing or protein-producing cells used to treat diseases, so the invention also is directed to the treatment of a disease without stimulation of host inflammatory cells by administering (1) an effective amount of a hormone-producing or protein-producing cell encapsulated in an alginate gel and (2) an effective amount of a BPI protein to inhibit stimulation of host inflammatory cells by alginate gel. The encapsulated hormone-producing or protein-producing cells and the BPI can be administered together in a single composition or as separate compositions.

The present invention provides a composition comprising a non-lipopolysaccharide and an effective amount of a bactericidal/permeability-increasing protein (BPI) to inhibit host inflammatory cell stimulation, with or without encapsulation in said non-lipopolysaccharide (non-LPS) of an enzyme, micro-organism or living cell, such as, a hormone-producing cell, and optionally a physiologically or pharmaceutically acceptable carrier. Kits are also provided for administration of the BPI and the non-LPS.

The compositions are useful for therapeutic, and prophylactic applications in vitro and in vivo. For therapy, a physiologically or pharmaceutically acceptable carrier is preferably present.

DETAILED DESCRIPTION OF THE INVENTION

Figure 1:
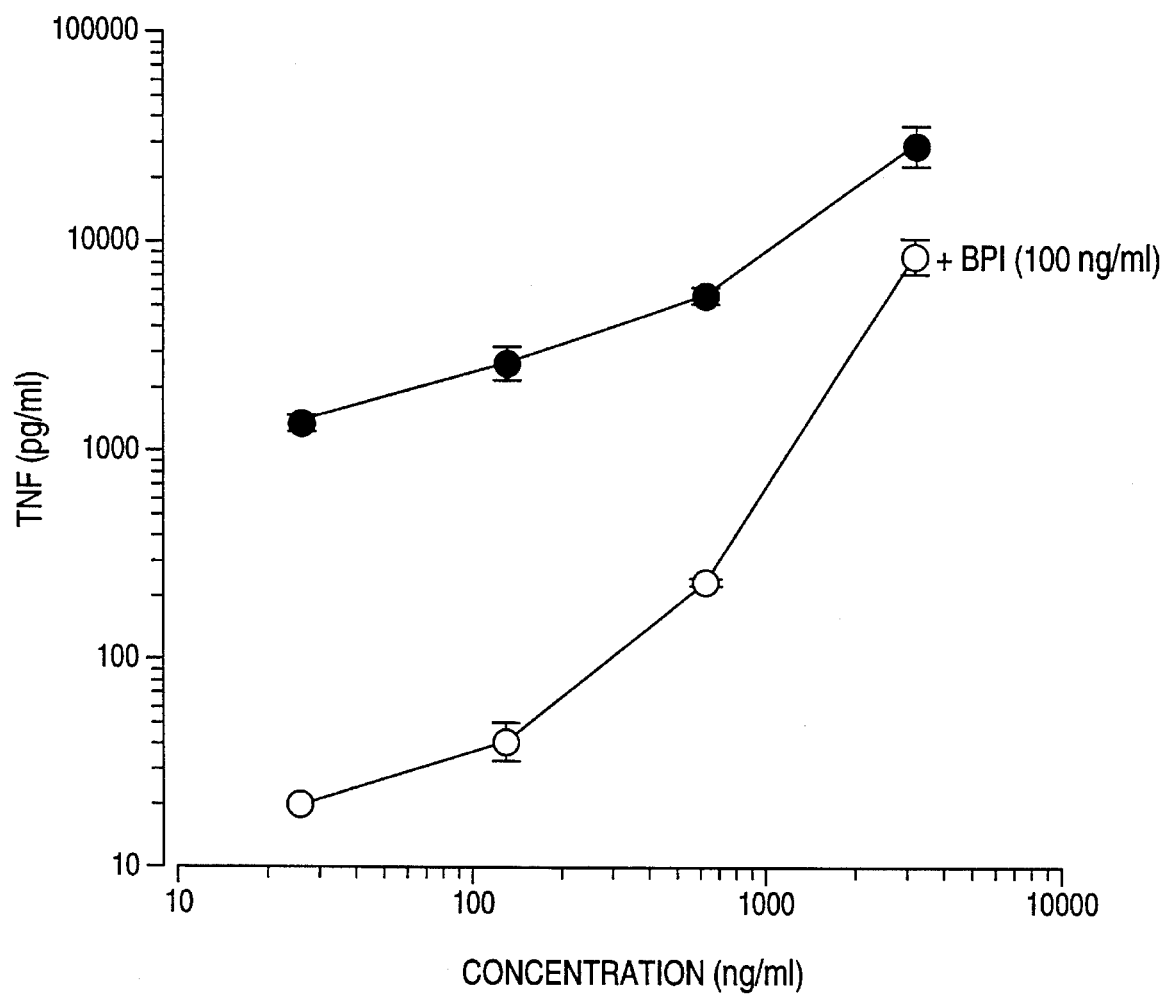
FIG. 1 is a graph of the results of an experiment of the effects of BPI on TNF production by macrophages induced by mannuronic acid polymer.

Before the present methods and compositions are described, it is to be understood that this invention is not limited to the particular compositions or methods described as such which those of skill in the art can, of course, vary. It is also to be understood that the terminology used herein is for the purpose of describing particular embodiments only, and is not intended to be limiting as to the scope of the present invention which will be limited only by the appended claims.

It should be noted that, as used in this specification and the appended claims, the singular forms "a" "an" and "the" include the plural referents unless the context clearly dictates otherwise. Thus, for example, reference to "an alginate" includes mixtures of alginates.

Unless defined otherwise, all technical and scientific terms used herein have the same meaning as commonly understood by one of ordinary skill in the art to which this invention belongs. Although any methods and materials similar or equivalent to those described herein can be useful in the practice or testing of the present invention, preferred methods and materials are described below. All publications and patents mentioned herein are incorporated herein by reference.

DEFINITIONS

For convenience, specific terminology of particular importance to the description of the present invention is defined below.

Bactericidal/permeability-increasing protein (BPI)

By "bactericidal/permeability-increasing protein" or "BPI" as used herein is meant (1) a BPI, (2) a biologically active fragment of BPI, (3) a biologically active analog of BPI, or (4) a biologically active variant of BPI, each of which can be in either recombinant or nonrecombinant form.

As used herein "BPI" also includes a native or naturally occurring biologically active 57 kd protein.

As used herein "biologically active polypeptide fragments of BPI" mean a polypeptide of molecular weight less than 57 kd, which prevents alginate from activating monocytes and provides a portion of the amino acid sequence present within BPI.

As used herein "biologically active polypeptide analog of BPI" means a polypeptide which prevents alginate from activating monocytes and has substantially the same amino acid sequence as, and the biological activity of, BPI. Biologically active polypeptide analogs of BPI include polypeptides, the sequence of which vary from the sequence of BPI by a change in amino acid sequence within the BPI sequence, e.g., a mutation, or addition of one or more amino acids at the amino- or carboxy-terminus, or both, of the BPI sequence.

As used herein "biologically active variant of BPI" means a polypeptide that (1) includes a portion of the amino acid sequence which is present within BPI and an amino acid sequence which is not present within BPI, and (2) has substantially the same biological activity, i.e. blocking alginate-mediated cytokine release by macrophages with BPI. Examples of such variants of BPI include those disclosed in co-pending U.S. application Ser. No. 08/165,717, filed Dec. 10, 1993, the disclosure of which is incorporated herein by reference.

As used herein "recombinant" means a polypeptide produced by genetic engineering methods. Thus, each of (1) BPI, (2) a biologically active fragment of BPI, (3) a biologically active analog of BPI, or (4) a biologically active variant of BPI can be in recombinant form. However, in the context of this application, BPI is not the same as recombinant BPI, the latter differing in some molecular characteristics from the native or naturally occurring polypeptide, e.g., in glycosylation pattern.

As used herein a "biologically active BPI" is one which prevents an alginate from stimulating macrophages or macrophage-like cells to release cytokines, such as IL-1, IL-6 or TNF.

Neutralization

By "neutralization," or "inhibition" of a non-lipopolysaccharide as used herein is meant the reduction or inhibition of the macrophage-like cell stimulation and cytokine production by a non-lipopolysaccharide by the administration of BPI. This includes the blocking of stimulation of cell production of cytokines, such as TNF, IL-1, IL-6 and the like.

Non-lipopolysaccharide

By "non-lipopolysaccharide" or "non-LPS" as used herein is meant a polysaccharide substantially free of lipid functionality. Suitable non-lipopolysaccharides include but are not limited to carbohydrates formed by the polymerization of many monosaccharide units, such as cellulose, starch, glycogen and the like.

Alginates

By "alginates" as used herein is meant a gel-forming polysaccharide composed of homopolymeric regions of beta-D-mannuronic (M) and alpha-L-glucuronic (G) acid also called "M-blocks" and "G-blocks", respectively, interspaced with regions of mixed sequence ("M-G-blocks"). The alginates include but are not limited to native or naturally-occurring alginates and synthetic alginates obtained by physical separation, direct chemical synthesis of polymers comprising beta-D-mannuronic acid and alpha-L-glucuronic acid or by culture of polysaccharide producing micro-organisms, using conventional techniques known to those of skill in the art. For example, U.S. Pat. No. 5,191,016 and Horcher et al., *Electrophoresis* (1992) 13(5):269–274 describe methods of synthesis or physical separation; and U.S. Pat. No. 3,856,625 describes production of alginate-type polysaccharides by cultivation of *Azotobacter vinelandii*. One preferred non-lipopolysaccharide is homopolymeric beta-1-4-1inked D-mannuronic acid (poly M) which can be derived from *Pseudomonas syringae pv. phaselicola* as described by Gross et al., *Phytopathol* (1987) 119:206. Another is High M alginate isolated from the intercellular substances of *Ascophyllum nodosum* as described by Haug et al., *Acta Chem Scand* (1967) 21:768.

The alginates include modified forms thereof, such as alginate-poly-L-lysines, described in *J Microencapsul (England)* (April–June 1991) 8(2):221–233; chemically cross-linked-1-3-beta-D-glucans described in Adachi et al., *Chem Pharm Bull (Tokyo)* (April 1990) 38(4):988–992. Alginates have gel-forming properties because divalent cations, including alkaline earth metals, such as calcium, barium, strontium, or heavy metal cation, bind to the G-blocks.

Encapsulation

By "encapsulation" or "entrapment" as used herein is meant entrapment within spheres of divalent cation alginate gel is a widely used technique for immobilization of enzymes, micro-organisms, living cells and the like. Encapsulation is conducted by conventional techniques known to those of skill in the art. For example, U.S. Pat. No. 4,950,600 describes methods for immobilizing such materials in an alginate gel without impairing the activity of the material encapsulated.

Microencapsulation of hormone-producing cells, such as pancreatic islet cells, in alginate gel has been used for treatment of diabetes mellitus, liver diseases, parathyroid diseases and the like. Peptide-producing cells or genetically-engineered microorganisms can also be used for treatment of hemophilia and other conditions.

Immunostimulation

By "immunostimulation" by a non-lipopolysaccharide as used herein is meant to stimulate host inflammatory cells and cytokine release in vitro or in vivo. Host inflammatory cells are any cells that release cytokines in response to alginates. Such cells include but are not limited to macrophages and monocytes.

By inhibition of immunostimulation by a non-lipopolysaccharide is meant to reduce or inhibit this immunostimulation process by administration of a BPI.

By "substantially-free" of inflammatory cell stimulation activity as used herein is meant that most to all of the inflammatory cell stimulation activity is inhibited, e.g. at least 75%, preferably at least 85% and especially at least 90% inhibited.

Bacterial lipopolysaccharide (LPS)

By "bacterial lipopolysaccharide" or "LPS" as used herein is meant a bacterial lipopolysaccharide or endotoxin, which is a glycolipid structural component of the bacterial cell wall, especially of enterobacteria. Chemically, they are composed of various specific polysaccharides linked to Lipid A. Lipid A contains rhamnose linked to galactosamine diphosphate which is esterified with myristic acid and is responsible for the cytokine-stimulating properties common to all LPS. "LPS" includes LPS, with and without the O-chain, and both rough and smooth LPS.

The present invention is directed to neutralization of non-lipopolysaccharide-mediated stimulation of host inflammatory cells by bactericidal permeability-increasing protein which comprises administering to a host, in the presence of a cell-stimulating amount of a non-lipopolysaccharide, with bactericidal/permeability-increasing protein in an amount effective to inhibit host inflammatory cell stimulation. The BPI activity can be used for both in vitro and in vivo applications for therapy or prophylactic treatment of endotoxin related responses.

The amount of BPI effective to inhibit host inflammatory cell stimulation will vary according to the amount and quality of the alginate as well as other conditions. The amount effective to inhibit host inflammatory cell stimulation is preferably from about 1% to about 100% by weight of the alginate. More BPI may need to be administered if it is slowly released from the gel.

Rabbit BPI is a neutrophil granule protein first discovered in 1975 [Weiss, J., et al., *J. Clin. Invest.*, 55:33 (1975)]. Human BPI was obtained in highly purified form from human neutrophils in 1978 and was shown to increase membrane permeability and have bactericidal activity against gram negative bacteria when assayed in phosphate buffered saline in vitro [Weiss, J., et al., *J. Biol. Chem.*, 253(8):2664–2672 (1978)]. Weiss et al. [*J. Biol. Chem.*, 254(21):11010–11014 (1979)] further showed that BPI increased phospholipase A2 activity suggesting a proinflammatory activity for BPI in addition to its in vitro bactericidal activity.

Rabbit BPI was purified in 1979 [Elsbach et al. *J. Biol. Chem.*, 254(21):11000–11009] and shown to have identical bactericidal and permeability increasing properties as BPI from humans providing a further source of material for study. Both BPI from rabbit and human were shown to be effective against a variety of gram negative bacteria in vitro, including K1- encapsulated *E. coli* [Weiss et al., *Infection and Immunity*, 38 (3) :1149–1153, (1982)].

Human BPI is a 57 kD protein which binds to the outer membrane of susceptible gram negative bacteria. [Weiss, et al. (1978)] The fact that BPI is a Lipid A binding protein is evidenced by: (1) rough strains of bacteria are more sensitive to both bactericidal and permeability increasing activities of BPI [Weiss, J., et al., *Infect. Immun.*, 51:594 (1986) ]; (2) mutations in Lipid A caused decreased binding and increased resistance to bactericidal activity of both polymyxin B and BPI [Farley, M. M., et al., *Infect. Immun.*, 56:1589 (1988)]; and (3) BPI competes with polymyxin B for binding to *S. typhimurium* (Farley 1988). BPI binding disrupts LPS structure, alters microbial permeability to small hydrophobic molecules and causes cell death (Weiss, et al. 1978).

In 1985 Ooi et al. reported that BPI retained its in vitro bactericidal activity after cleavage by neutrophil proteases, suggesting that fragments of the molecule retain activity (Ooi and Elsbach, *Clinical Research*, 33 (2):567A (1985). The in vitro bactericidal and permeability increasing activities of BPI were present in the N-terminal 25 kD fragment of the protein. (Ooi, C. E., et al., *J. Biol. Chem.*, 262:14891 (1987).

BPI binds LPS and inhibits neutrophil and monocyte activation [Marra et al., *J. Immunol.*, 144:662–666 (1990); Marra and Scott, WO90/09183, published 23 Aug. 1990; Fisher et al., *Circulatory Shock*, 34: 120 (1991); Marra et al., *Blood Purif.*, 11:134–140 (1993); Fisher et al., *Crit. Care Med.*, 22:553–558 (1994); Marra et al., *Crit. Care Med.*, 22:559–565 (1994)].

BPI shares amino acid sequence homology and immunocrossreactivity to another endotoxin binding protein termed Lipopolysaccharide Binding Protein (LBP) [Tobias et al., *J. Biol. Chem.*, 263(27):13479–13481 (1988)]. LBP-LPS complexes bind to monocyte cell surface receptors (CD 14), which results in increased synthesis and release of the inflammatory cytokine tumor necrosis factor (TNF) [Schumann et al., *Science*, 249:1429–1431]. Thus, LBP promotes the immunostimulatory activities of LPS. BPI has exactly the opposite effect of LBP.

A cDNA encoding BPI was obtained and sequenced by Gray et al. [Gray et al., *Clin. Res.*, 36:620A (1988) and Gray et al., *J. Biol. Chem.*, 264(16):9505–9506 (1989)]. Marra et al. reported that BPI is released by neutrophils in its full-length form after the neutrophils are stimulated in vitro (*J. Immunology*, 148:532–537 (1992)). Circulating BPI levels increase during sepsis in vivo. (Calvano et al., *Arch. Surg.*, 129:220–226 (1994)).

The present invention provides for use of soluble BPI in active form as described in Marra, U.S. Pat. No. 5,234,912. The present invention includes the use of isolated molecular forms of BPI, such as the glycosylated and nonglycosylated forms of the molecule, as described in the '912 patent, which appear to have different serum half-life profiles in vivo and thus different therapeutic potential. BPI from neutrophils is a mixture of the glycosylated and nonglycosylated forms.

Pancreatic islet cells are one preferred embodiment of the application of the present invention. However, other cells, including but not limited to Factor VIII-producing hepatic cells and recombinantly engineered bacterias, can be used in the invention.

The non-lipopolysaccharides can comprise an alginate gel used to immobilize enzymes, micro-organisms, living cells, cell organelles, cell fractions and the like, such as hormone-producing or protein-producing cells used to treat diseases. Since alginates are potent simulators of cytokines such as TNF, IL-1, and IL-6, the invention can be used for any application of alginates in which it is desirable to inhibit the production of cytokines. TNF-alpha and IL-1 are inflammatory cytokines with potent fibroblast growth activity (LeJ. Vilcek, J. *Lab Invest* (1987) 56:234). The M-block and M-G-block alginates promote cytokine production (Otterlei et al., *J Immunotherapy* (1991) 10:286–291). Thus, alginate gels of the invention used as a matrix for implanted cells in vivo will be blocked from causing inflammatory reactions when BPI is administered in their presence. As mentioned previously, entrapment within spheres of calcium alginate gel is a widely used technique for immobilization of living cells (Scott, C. D., *Enzyme Microb Technol* (1987) 9:66). Microencapsulation of hormone-producing cells in calcium alginate has been used for treatment of diabetes mellitus (Lim et al., *Science* (1980) 21:908; O'Shea et al., *Biochem Biophys Acta* (1984) 804:133; Goosen et al., *Biotech Bioeng* (1985) 27:146; Sun et al., "Topics in pharmaceutical science", Amsterdam, Elsevier Science Publishers B.V. (1985) p. 93; Sun, et al., *CRC Crit Rev Ther Drug Carrier Sys* (1987) 4:1–12; and Tze et al., *Transplantation* (1982) 33:563); liver diseases (Miura et al., *Artif Organs* (1986) 10:460 and Tompkins et al., *Biotechnol Bioeng* (1988) 31:11); and parathyroid diseases (Darquay et al., *Trans Am Soc Artif Inter Organs* (1987) 33:365).

The invention is also directed to inhibiting non-lipopolysaccharides-mediated tumor necrosis factor (TNF), interleukin-like hormone-1 (IL-1) and IL-6 production by human host mononuclear cells in the presence of a cell-stimulating amount of a non-lipopolysaccharide which comprises administering to a host BPI protein in an amount effective to inhibit TNF, IL-1 and IL-6 production.

The invention also is directed to the treatment of a disease in a subject by administering (1) an effective amount of a hormone-producing or protein-producing cell encapsulated in an alginate gel and (2) an effective amount of a BPI to inhibit stimulation of inflammatory cells by the alginate gel. The encapsulated hormone-producing or protein-producing cells and the BPI can be administered together in a single composition or as separate materials. While the subject or host is preferably a human, other warm-blooded animals, including canines, felines and the like, which are afflicted with diabetes, liver diseases and parathyroid diseases can also be similarly treated with the methods and compositions of the invention.

Formulations

The present invention provides compositions for the above uses.

Preferably, a BPI protein is used in a composition which comprises the BPI and a carrier. A pharmaceutically acceptable carrier is preferred for use in medical products designed for internal use.

As used in this application, a physiologically or pharmaceutically acceptable carrier encompasses gelatin (including alginates), and any of the standard carriers, such as sterile solutions. The carriers can also include color additives, detergents, and the like.

Compositions comprising carriers are formulated by following procedures well known in the art. However, the composition comprising BPI in an amount sufficient to inhibit non-lipopolysaccharide stimulation of monocytes is previously unknown. The amount of BPI to inhibit non-LPS can be readily determined by those of skill in the art by assaying for inhibition of any non-LPS stimulation with various amounts of BPI following the teachings of the invention.

The present invention provides a composition comprising a non-lipopolysaccharide (non-LPS) TNF-stimulating compound such as an alginate and an effective amount of a BPI protein to inhibit inflammatory cell stimulation by the non-LPS, with or without encapsulation in the non-lipopolysaccharide of an enzyme, microorganism or living cell, such as, a hormone-producing or protein-producing cell, and optionally a physiologically or pharmaceutically acceptable carrier. The BPI can be mixed into the gel or coated on the outside.

The compositions are useful for therapeutic or prophylactic applications in vitro and in vivo. For therapy, a physiologically or pharmaceutically acceptable carrier is preferably present.

BPI also can be administered after the gel is implanted. Then the method of administration of the BPI is preferably effected by well known systemic methods, including, but not limited to, intravenous, intramuscular, subcutaneous methods and the like.

In the compositions of this invention, the amount of BPI and/or non-LPS stimulant incorporated into the composition for their respective functions can vary widely. Methods of determining the precise amount are well known to those of skill in the art and depend inter alia upon the subject being treated, the specific pharmaceutical carrier, the route of administration being used, and the frequency with the BPI is administered.

The invention further includes a method for preparing an alginate-encapsulated living cell composition substantially free of inflammatory cell stimulation activity, which comprises encapsulating living cells in an alginate gel and admixing the gel with a BPI, optionally with a physiologically or pharmaceutically acceptable carrier.

The invention also includes a kit for administration of a non-lipopolysaccharide substantially free of inflammatory cell-stimulating activity comprising (a) a BPI and (b) a non-lipopolysaccharide, optionally having encapsulated therein an enzyme, microorganism, living cells or cell fractions, wherein the BPI and non-lipopolysaccharide can be administered together or separately.

EXAMPLES

The invention is illustrated by the following examples which should not be regarded as limiting the invention in any way. Unless otherwise specified, the experiments were conducted at temperatures of 37° C. and ambient pressures.

Example 1

Use of BPI to block macrophage stimulation with a variety of reagents

Methods and Materials

Polysaccharides, antibodies, LPS and LBP

Homopolymeric β1-4-1inked D-mannuronic acid (Poly M) was derived from *Pseudomonas acruginosa* DE127 (Sigma) as described by Gross and Rudolph, *J. Phytopathol.* (1987) 119:206. Briefly, the extracellular polysaccharide from liquid cultures of *Pseudomonas acruginosa* was prepared and purified by ion exchange chromatography to remove LPS. Before use, the poly M preparation was filtered twice through an endotoxin-removing filter purchased from AllerCheck (Portland, Me.). High M alginate was isolated from the intracellular substances of *Ascophyllum modosum* fruiting bodies as described by Haug et al. *Acta Chem. Scand.* (1987) 21:768. The β1-4-linked glucuronic acid (D-GlcA; C60XY) was prepared by oxidation of cellulose at position C-6 (A. Flaibani, personal communication). The degree of oxidation (94%) was determined by potentiometric titration (Nevell, T. F. *Methods Carbohydr. Chem.* (1963) 3:161 and Yackel et al., *J. Am. Chem. Soc.* (1942) 84:121). The monomer composition and sequential arrangement of the different polysaccharides were analyzed by $^1$H-NMR spectroscopy on a Burker 400 WM spectrometer as described previously Grasdalen et al., *Carbohyr. Res.* (1979) 68:23 and Grasdalen, H., *Carbohydr. Res.* (1983) 118:255. The molecular weight of the different polysaccharides was estimated from intrinsic viscosity measurements in an automatic dilution viscosity system (Scott-Gerate) using the Mark Houwink Sakurada equation (Hardling et al., *Advances in Carbohydrate Chemistry* JAI press, London (1991) p63). The different polysaccharides were diluted in PBS and sterile filtered through a 0.2-μm filter (Nuclepore, Pleasanton, Calif.) before use. Endotoxin contamination in the different polysaccharides was measured by the LAL assay (Kabi Viotrum, Stockholm, Sweden). The poly M had an endotoxin level of about 15 ng/mg.

Cells and cell cultures

Monocytes were isolated from human A+ blood buffy coat (The Bloodbank, University of Trondheim, Norway) as described by Boyum, A. M., *Sand. J. Immunol.* (1976) 5:9. Monolayers of monocytes in 24-well culture plates (Costar, Cambridge, Mass.) were cultured in complete medium consisting of RPMI 1640 (Gibco, Paisley, GB) with 1% glutamine, 40 μg/ml gentamicin, and 25% A+ serum (The Bloodbank, University of Trondheim). In some experiments monocytes were isolated and cultivated in AIM serum-free medium (Gibco). Different concentrations of polysaccharides were harvested 4–6 h later and assayed for TNF activity in the WEHI 164 clone 13 bioassay (Espevik et al., *J. Immunol. Methods.* (1986) 95:99).

The reagents were added to human monocytes in the presence of 10% human serum in RPMI 1640. After about 4–6 h, the supernatants were harvested and assayed for TNF bioactivity using the WEHI 164 clone 13 assay.

FIG. 1 is a graph of the results of an experiment of the effects of BPI on TNF production by macrophages induced by polymannuronic acid. The upper line (dark circles) demonstrates TNF release in response to increasing mannuronic acid concentration. The bottom line (clear circles) demonstrates that 100 ng/ml of BPI substantially reduced TNF release.

The data demonstrate that BPI neutralized poly M-mediated stimulation of TNF release from monocytes.

Example 2

The experiment of Example 1 was repeated with different doses of BPI to test inhibition of the test materials on TNF production from human monocytes which were induced by polymannuronic acid (poly M).

Figure 2:
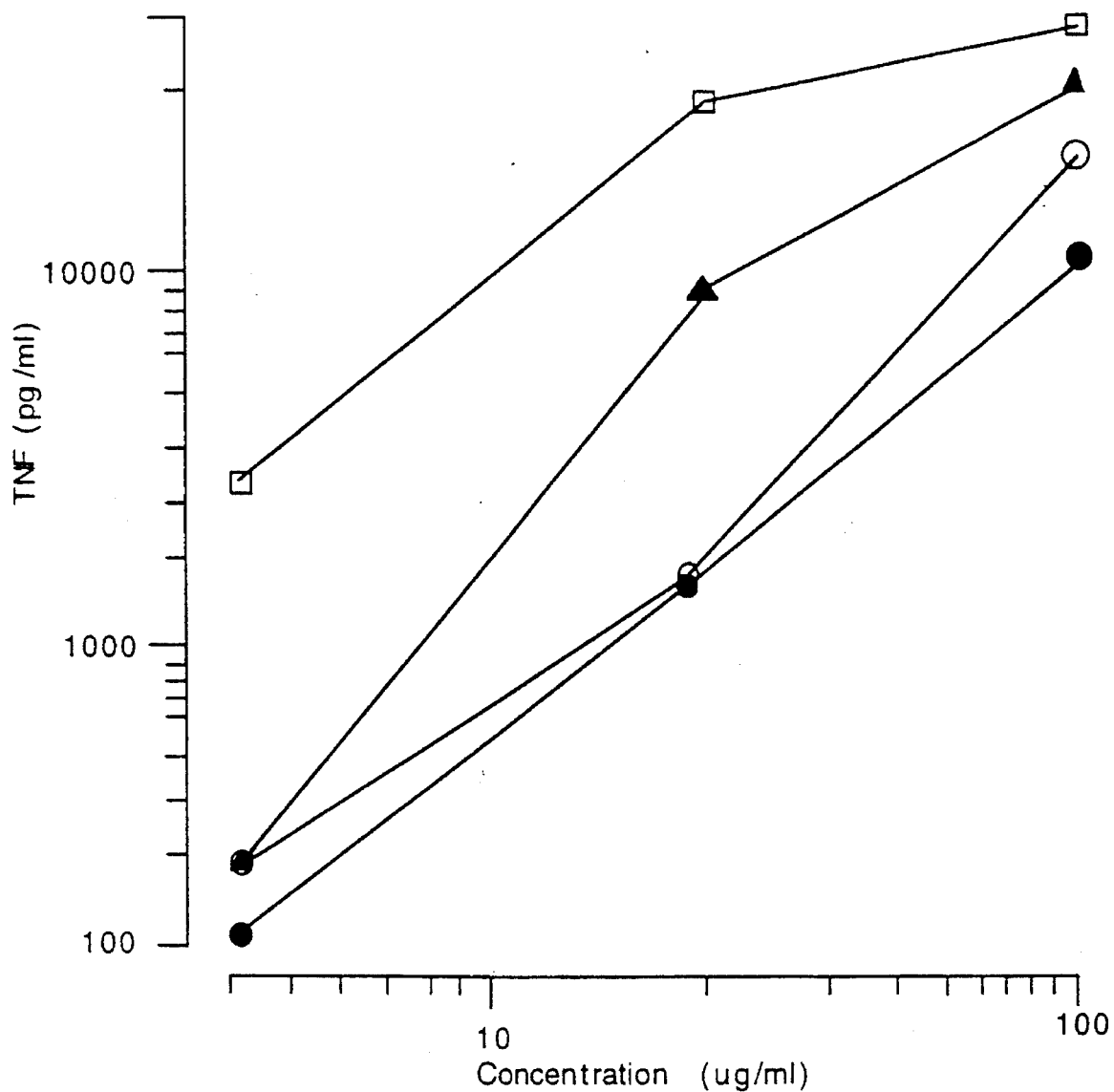
FIG. 2 is a graph of an experiment on the effects of different doses of BPI on poly M-induced TNF production.

FIG. 2 is a graph of an experiment on the effects of BPI on poly M-induced TNF production. In the graph, the open square represents poly M, the solid circle represents poly M plus 1 μg/ml of BPI, the open circle represents poly M plus 0.1 μg/ml of BPI, and the solid triangle represents poly M plus 0.01 μg/ml of BPI.

The data demonstrate that BPI inhibited TNF production by poly M. At the lowest concentration of poly M (4 micrograms/ml), all three concentrations of BPI (even 0.01 micrograms/ml BPI) inhibited the TNF response by more than 90%. At the lowest concentration of poly M which gave the maximal TNF response (about 20 micrograms/ml), more than 90% inhibition was observed using only 0.1 microgram/ml BPI. At the highest concentration of poly M (100 microgram/ml, five fold higher than the concentration required to give maximal TNF response), the low concentrations of BPI used in this experiment were not effective.

Example 3

Pancreatic islet cells are inserted into an alginate gel and used to test for the inhibition of non-LPS-mediated stimulation of host inflammatory cells in intraperitoneal transplantation of the microencapsulated islet cells. The gel is coated with different doses of BPI. BPI doses ranging from about 0.5% of the weight of the gel to about equal to the weight of the gel are used. Alternatively, a range of doses of BPI diluted in RPMI 1640 are administered separately.

The administered BPI serves to prevent an inflammatory reaction to the implant.

We claim:

1. A method of inhibiting mannuronic acid polymer-mediated stimulation of host inflammatory cells in the presence of a cell-stimulating amount of a mannuronic acid polymer, said method comprising administering to the host bactericidal/permeability-increasing protein (BPI) in an amount effective to inhibit inflammatory cell stimulation.

2. The method of claim 1 wherein the mannuronic acid polymer comprises a gel having encapsulated therein living implant cells, and an effective amount of BPI to inhibit stimulation of said inflammatory cell by said gel, said effective amount being from about 1% to 100% by weight of the mannuronic acid polymer.

3. The method of claim 2 wherein the gel encapsulated cells are hormone-producing cells.

4. The method of claim 3 wherein the hormone-producing cells and the BPI are administered together in a single composition or separate compositions.

5. The method of claim 3 wherein the hormone-producing cells are pancreatic islet cells.

6. A method of inhibiting mannuronic acid polymer-mediated tumor necrosis factor (TNF), IL-1 or IL-6 production by human host mononuclear cells in the presence of a cell-stimulating amount of a mannuronic acid polymer, which comprises administering to a host bactericidal/permeability-increasing protein in an amount effective to inhibit TNF, IL-1 or IL-6 production.

7. The method of claim 6 wherein the mannuronic acid polymer comprises a gel having encapsulated therein living cells and an effective amount of a BPI to inhibit stimulation of said cells by said gel, said effective amount of BPI being from about 1% to 100% by weight of the mannuronic acid polymer.

8. A composition comprising a mannuronic acid polymer and an effective amount of a bactericidal/permeability-increasing protein (BPI) to inhibit inflammatory cell stimulation by said mannuronic acid polymer, and optionally a physiologically or pharmaceutically acceptable carrier.

9. The composition of claim 8 wherein said mannuronic acid polymer is a gel having encapsulated therein living cells.

10. The composition of claim 8, wherein said effective amount is from about 1% to 100% by weight of the mannuronic acid polymer.

11. A method for preparing an encapsulated living cell composition substantially-free of inflammatory cell stimulation activity, which comprises (a) encapsulating living cells in a mannuronic acid polymer gel and (b) admixing said gel with a bactericidal/permeability-increasing protein (BPI) optionally with a physiologically or pharmaceutically acceptable carrier.

12. A kit for administration of a mannuronic acid polymer substantially free of inflammatory cell stimulation activity comprising (a) a bactericidal/permeability-increasing protein (BPI) and (b) a mannuronic acid polymer, wherein said (a) and (b) can be administered together or separately.

13. The kit of claim 12 wherein said mannuronic acid polymer has encapsulated therein living cells.

* * * * *